United States Patent [19]

Christensen, IV et al.

[11] Patent Number: 5,605,923

[45] Date of Patent: Feb. 25, 1997

[54] COMPOUNDS USEFUL FOR TREATING INFLAMMATORY DISEASES AND INHIBITING PRODUCTION OF TUMOR NECROSIS FACTOR

[75] Inventors: Siegfried B. Christensen, IV, Philadelphia; Cornelia J. Forster, Bensalem, both of Pa.

[73] Assignee: SmithKline Beecham Corporation, Philadelphia, Pa.

[21] Appl. No.: 313,093

[22] PCT Filed: Mar. 5, 1993

[86] PCT No.: PCT/US93/02516

§ 371 Date: Sep. 29, 1994

§ 102(e) Date: Sep. 29, 1994

[87] PCT Pub. No.: WO93/19751

PCT Pub. Date: Oct. 14, 1993

Related U.S. Application Data

[63] Continuation-in-part of Ser. No. 968,761, Oct. 30, 1992, abandoned, which is a continuation-in-part of Ser. No. 862,111, Apr. 2, 1992, abandoned.

[51] Int. Cl.$^6$ ..................... A61K 31/275; C07C 255/50
[52] U.S. Cl. ..................... 514/417; 514/520; 514/521; 514/523; 514/719; 514/886; 548/473; 548/480; 558/426; 568/646
[58] Field of Search ..................... 514/417, 520, 514/521, 523, 719, 886; 548/473, 480; 558/426; 568/646

[56] References Cited

PUBLICATIONS

Chemical Abstracts, vol. 115, No. 1, abstract 8542s, 1991.
Chemical Abstracts, vol. 90, No. 11, abstract 86895p, 1979.
Chemical Abstracts, vol. 99, No. 1, abstract 5272u, 1983.

*Primary Examiner*—Jacqueline Haley
*Attorney, Agent, or Firm*—James M. Kanagy; Stephen Venetianer; Edward T. Lentz

[57] ABSTRACT

Novel cyclohexene-ylidene derivatives of formula (I) are described herein. These compounds inhibit the production of Tumor Necrosis Factor and are useful in the treatment of disease states mediated or exacerbated by TNF production; they are also useful in the mediation or inhibition of enzymatic or catalytic activity of phosphodiesterase IV and are therefore useful in the treatment of disease states in need of mediation or inhibition thereof.

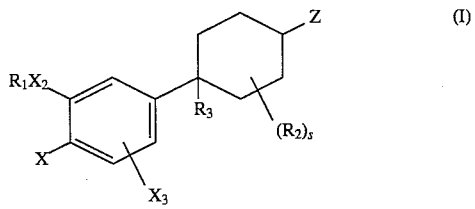

6 Claims, No Drawings

COMPOUNDS USEFUL FOR TREATING INFLAMMATORY DISEASES AND INHIBITING PRODUCTION OF TUMOR NECROSIS FACTOR

This is a National Stage Application of PCT/US93/02516, filed 5 Mar. 1993 and published as WO93/19751, on 14 Oct. 1993 which is a continuation-in-part of U.S. Ser. No. 07/968,761, filed Oct. 30, 1992, now abandoned, which is a continuation-in-part of U.S. Ser. No. 07/862,111, filed Apr. 2, 1992, now abandoned.

FIELD OF INVENTION

The present invention relates to novel compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et at., The Immunopathogenesis of HIV Infection, Advances in Immunology, Vol. 57, 1989]. Monokines, such as TNF, have been shown to activate HIV replication in monocytes and/or macrophages [See Poli et at., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically Candida albicans has been shown to induce TNF production in vitro in human monocytes and natural killer cells. [See Riipi et at., Infection and Immunity, 58(9):2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214, 1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

This invention relates to the novel compounds of Formula (I) which are useful in the mediation or inhibition of the enzymatic activity (or catalytic activity) of phosphodiesterase IV (PDE IV). The novel compounds of Formula (I) also have Tumor Necrosis Factor (TNF) inhibitory activity.

This invention also relates to the pharmaceutical compositions comprising a compound of Formula (I) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I), as shown below.

The invention further provides a method for the treatment of allergic and inflammatory disease which comprises administering to a mammal, including humans, in need thereof, an effective amount of a compound of Formula (I). The invention also provides a method for the treatment of asthma which comprises administering to a mammal, including humans, in need thereof, an effective amount of a compound of Formula (I).

This invention also relates to a method of inhibiting TNF production in a mammal, including humans, which method comprises administering to a mammal in need of such treatment, an effective TNF inhibiting amount of a compound of Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I).

The compounds of Formula (I) are also useful in the treatment of additional viral infections, where such viruses are sensitive to upregulation by TNF or will elicit TNF production in vivo.

The compounds of Formula (I) are also useful in the treatment of yeast and fungal infections, where such yeast and fungi are sensitive to upregulation by TNF or will elicit TNF production in vivo.

The novel compounds of this invention are represented by the structure:

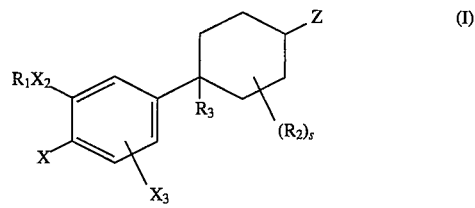

wherein:

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;

m is 0 to 2;

n is 1 to 4;

r is 1 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in $-(CR_4R_5)_nO(CR_4R_5)_mR_6$;

X is $YR_2$, halogen, nitro, $NR_4R_5$, or formyl amine;

Y is O or $S(O)_{m'}$;

m' is a number having a value of 0, 1, or 2;

$X_2$ is O or $NR_8$;

$X_3$ is hydrogen or X;

$R_2$ is independently selected from $-CH_3$ or $-CH_2CH_3$ optionally substituted by 1 or more halogens;

s is 0 to 4;

$R_3$ is hydrogen, halogen, $C_{1-4}$ alkyl, halo-substituted $C_{1-4}$ alkyl, $CH_2NHC(O)C(O)NH_2$, $-CH=CR_8R_{8'}$, cyclopropyl optionally substituted by $R_{8'}$, CN, $OR_8$, $CH_2OR_8$, $NR_8R_{10}$, $CH_2NR_8R_{10}$, $C(Z')H$, $C(O)OR_8$, $C(O)NR_8R_{10}$, or $C\equiv CR_{8'}$;

Z' is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$;

Z is $OR_{14}$, $OR_{15}$, $SR_{14}$, $S(O)_mR_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

Y' is O or S;

$R_7$ is $-(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, $-F$, $-Br$, $-Cl$, $-NO_2$, $-NR_{10}R_{11}$, $-C(O)R_8$, $-C(O)OR_8$, $-OR_8$, $-CN$, $-C(O)NR_{10}R_{11}$, $-OC(O)NR_{10}R_{11}$, $-OC(O)R_8$, $-NR_{10}C(O)NR_{10}R_{11}$, $-NR_{10}C(O)R_{11}$, $-NR_{10}C(O)OR_9$, $-NR_{10}C(O)R_{13}$, $-C(NR_{10})NR_{10}R_{11}$, $-C(NCN)NR_{10}R_{11}$, $-C(NCN)SR_9$, $-NR_{10}C(NCN)SR_9$, $-NR_{10}C(NCN)NR_{10}R_{11}$, $-NR_{10}S(O)_2R_9$, $-S(O)_mR_9$, $-NR_{10}C(O)C(O)NR_{10}R_{11}$, $-NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is independently selected from hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

$R_{15}$ is $C(O)R_{14}$, $C(O)NR_4R_{14}$, $S(O)_2R_7$, or $S(O)_2NR_4R_{14}$;

provided that:

f) when Z is OH, X is $YR_2$, Y is oxygen, $X_2$ is oxygen, $X_3$ is hydrogen, s is 0, $R_2$ is $CH_3$ in $YR_2$, and $R_1$ is $CH_3$, then $R_3$ is other than CN or COOH;

g) when Z is OH, or $OCH_3$, $X_2$ is oxygen, $X_3$ is hydrogen, s is 0, and X is $YR_2$, then $R_3$ is other than H;

h) when Z is $OS(O)_2C_{1-6}$ alkyl or $OS(O)_2$ aryl, $X_2$ is oxygen, $X_3$ is hydrogen, s is 0, then $R_3$ is other than $OR_8$;

i) when $R_{12}$ is N-pyrazolyl, N-imidazolyl, N-triazolyl, N-pyrrolyl, N-piperazinyl, N-piperidinyl, or N-morpholinyl, then q is not 1; or j). when Z is OH or $OSO_2R_7$ and $R_3$ is $CH_3$, CHOH or $CH_2OC_{1-3}$ alkyl, then $R_1X_2$ is not $C_{1-3}$ alkoxy and X is not halogen, methoxy, ethoxy, methylthio or ethylthio;

k) when Z is $-NH_2$, $NH(C_{1-3}$ alkyl), $N(C_{1-3}$ alkyl)$_2$, $NH(CH_2)_{2-5}C(O)Ar$ where Ar is naphthyl or phenyl or Z is unsubstituted or substituted pyrrolidinyl, piperidinyl, morpholinyl or piperazinyl and $R_3$ is $CH_3$, CHOH or $CH_2OC_{1-3}$ alkyl, then $R_1X_2$ is not $C_{1-3}$ alkoxy and X is not halogen, methoxy, ethoxy, methylthio or ethylthio;

or the pharmaceutically acceptable salts thereof.

DETAILED DESCRIPTION OF THE INVENTION

This invention relates to the novel compounds of Formula (I), and to pharmaceutical compositions comprising a compound of Formula (I) and a pharmaceutically acceptable carrier or diluent. This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulceralive colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus, [Kidney Int., 37:362, 1990; Kidney Int., 35:494, 1989] and central nervous system disorders such as depression and multi-infarct dementia.

The compounds of Formula (I) are also useful in the treatment of vital infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibitors of Formula (1). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

The compounds of Formula (I) are also useful in the treatment of yeast and fungal infections, where such yeast and fungi are sensitive to upregulation by TNF or will elicit TNF production in vivo. A preferred disease state for treatment is fungal meningitis. Additionally, the compounds of Formula (I) may be administered in conjunction with other drugs of choice for systemic yeast and fungal infections. Drugs of choice for fungal infections, include but are not limited to, the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The co-administration of the anti-fungal agent with a compound of Formula (I) may be in any preferred composition for that compound such as is well known to those skilled in the art, for instance the various Amphotericin B formulations. Co-administration of an anti-fungal agent with a compound of Formula (I) may mean simultaneous administration or in practice, separate administration of the agents to the mammal but in a consecutive manner. In particular, the compounds of Formula (I) may be co-administered with a formulation of Amphotericin B, notably for systemic fungal infections. The preferred organism for treatment is the Candida organism. The compounds of Formula (I) may be co-administered in a similar manner with anti-vital or antibacterial agents.

The compounds of Formula (I) may also be used for inhibiting and/or reducing the toxicity of an anti-fungal, anti-bacterial or anti-vital agent by administering an effective amount of a compound of Formula (I) to a mammal in need of such treatment. Preferably, a compound of Formula (I) is administered for inhibiting or reducing the toxicity of the Amphotericin class of compounds, in particular Amphotericin B. The preparation of a pharmaceutically acceptable salt will be determined by the nature of the compound itself, and can be prepared by conventional techniques readily available to one skilled in the art.

When $R_1$ is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) are $CH_2$-cyclopropyl, $CH_2$-$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}$C(O)O$(CH_2)_{0-2}$CH$_3$, —$(CH_2)_{1-3}$O$(CH_2)_{0-2}$CH$_3$, and —$(CH_2)_{2-4}$OH.

When $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH$(—$CH_3$)—, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published 5 Nov. 1987, whose disclosure is incorporated herein by reference in its entirety.

Z is preferably OR$_{14}$, OR$_{15}$, SR$_{14}$, S(O)$_m$R$_7$, S(O)$_2$NR$_{10}$R$_{14}$, NR$_{10}$R$_{14}$, NR$_{14}$C(O)R$_9$, NR$_{10}$C(O)R$_{14}$, NR$_{10}$C(O)OR$_7$, NR$_{10}$C(O)NR$_{10}$R$_{14}$, NR$_{10}$S(O)$_2$NR$_{10}$R$_{14}$, NR$_{10}$C(NCN)NR$_{10}$R$_{14}$, NR$_{10}$S(O)$_2$R$_7$, NR$_{10}$C(CR$_4$NO$_2$)NR$_{10}$R$_{14}$, NR$_{10}$C(NCN)SR$_9$, NR$_{10}$C(CR$_4$NO$_2$)SR$_9$, NR$_{10}$C(NR$_{10}$)NR$_{10}$R$_{14}$, NR$_{10}$C(O)C(O)NR$_{10}$R$_{14}$, or NR$_{10}$C(O)C(O)OR$_{14}$; most preferred are those compounds wherein the R$_{14}$ group of Z is R$_4$.

Preferred X groups for Formula (I) are those wherein X is YR$_2$ and Y is oxygen. The preferred $X_2$ group for Formula (I) is that wherein $X_2$ is oxygen. The preferred $X_3$ group for Formula (I) is that wherein $X_3$ is hydrogen. Preferred R$_2$ groups, where applicable, is a $C_{1-2}$ alkyl optionally substituted by 1 or more halogens. The halogen atoms are preferably fluorine and chlorine, more preferably fluorine. More preferred R$_2$ groups are those wherein R$_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred R$_3$ moieties are C(O)NH$_2$, CH$_2$NHC(O)C(O)NH$_2$, C≡R$_8$, CN, C(Z')H, CH$_2$OH, CH$_2$F, CF$_2$H, and CF$_3$. More preferred are C≡CH and CN. Z' is preferably O or NOR$_8$.

Preferred R$_7$ moieties include optionally substituted —(CH$_2$)$_{1-2}$(cyclopropyl), —(CH$_2$)$_{0-2}$(cyclobutyl), —(CH$_2$)$_{0-2}$(cyclopentyl), —(CH$_2$)$_{0-2}$(cyclohexyl), —(CH$_2$)$_{0-2}$(2-, 3- or 4-pyridyl), (CH$_2$)$_{1-2}$(2-imidazolyl), (CH$_2$)$_{0-2}$(4-morpholinyl), (CH$_2$)$_2$(4-piperazinyl), (CH$_2$)$_{1-2}$(2-thienyl), (CH$_2$)$_{1-2}$(4-thiazolyl), and (CH$_2$)$_{0-2}$phenyl;

Preferred rings when R$_{10}$ and R$_{11}$ in the moiety —NR$_{10}$R$_{11}$ together with the nitrogen to which they are attached form a 5 to 7 membered ring optionally containing at least one additional heteroatom selected from O, N, or S include, but are not limited to 1-imidazolyl, 2-(R$_8$)-1-imidazolyl, 1-pyrazolyl, 3-(R$_8$)-1-pyrazolyl, 1-triazolyl, 2-triazolyl, 5-(R$_8$)-1-triazolyl, 5-(R$_8$)-2-triazolyl, 5-(R$_8$)-1-tetrazolyl, 5-(R$_8$)-2-tetrazolyl, 1-tetrazolyl, 2-tetrazloyl, morpholinyl, piperazinyl, 4-(R$_8$)-1-piperazinyl, or pyrrolyl ring.

Preferred rings when R$_{10}$ and R$_{14}$ in the moiety —NR$_{10}$R$_{14}$ together with the nitrogen to which they are attached may form a 5 to 7 membered ring optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety R$_7$ as described herein for Formula (I). Illustrations of such carbon substitutions includes, but is not limited to, 2-(R$_7$)-1-imidazolyl, 4-(R$_7$)-1-imidazolyl, 5-(R$_7$)-1-imidazolyl, 3-(R$_7$)-1-pyrazolyl, 4-(R$_7$)-1-pyrazolyl, 5-(R$_7$)-1-pyrazolyl, 4-(R$_7$)-2-triazolyl, 5-(R$_7$)-2-triazolyl, 4-(R$_7$)-1-triazolyl, 5-(R$_7$)-1-triazolyl, 5-(R$_7$)-1-tetrazolyl, and 5-(R$_7$)-2-tetrazolyl. Applicable nitrogen substitution by R$_7$ includes, but is not limited to, 1-(R$_7$)-2-tetrazolyl, 2-(R$_7$)-1-tetrazolyl, 4-(R$_7$)-1-piperazinyl. Where applicable, the ring may be substituted one or more times by R$_7$.

Preferred groups for NR$_{10}$R$_{14}$ which contain a heterocyclic ring are 5-(R$_{14}$)-1-tetrazolyl, 2-(R$_{14}$)-1-imidazolyl, 5-(R$_{14}$)-2-tetrazolyl, 4-(R$_{14}$)-1-piperazinyl, or 4-(R$_{15}$)-1-piperazinyl.

Preferred rings for R$_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the R$_7$ group is optionally substituted by a heterocyclic ring such as imidazolyl, pyrazolyl, triazolyl, tetrazolyl, or thiazolyl, the heterocyclic ring itself may be optionally substituted by R$_8$ either on an available nitrogen or carbon atom, such as 1-(R$_8$)-2-imidazolyl, 1-(R$_8$)-4-imidazolyl, 1-(R$_8$)-5-imidazolyl, 1-(R$_8$)-3-pyrazolyl, 1-(R$_8$)-4-pyrazolyl, 1-(R$_8$)-5-pyrazolyl, 1-(R$_8$)-4-triazolyl, or 1-(R$_8$)-5-triazolyl. Where applicable, the ring may be substituted one or more times by R$_8$.

Preferred are those compounds of Formula (I) wherein R$_1$ is —CH$_2$-cyclopropyl, —CH$_2$-C$_{5-6}$ cycloalkyl, —C$_{4-6}$ cycloalkyl, tetrahydrofuran-3-yl, (3- or 4-cyclopentenyl), benzyl or —C$_{1-2}$ alkyl optionally substituted by 1 or more fluorines, and —(CH$_2$)$_{2-4}$ OH; R$_2$ is methyl or fluoro-substituted alkyl, R$_3$ is CN or C≡CR$_8$; and X is YR$_2$.

Most preferred are those compounds wherein R$_1$ is —CH$_2$-cyclopropyl, cyclopentyl, methyl or CF$_2$H; R$_3$ is CN or C≡CH; X is YR$_2$; Y is oxygen; X$_2$ is oxygen; X$_3$ is hydrogen; and R$_2$ is CF$_2$H or methyl.

A preferred subgenus of Formula (I) is the compounds of Formula (Ia) and (Ib)

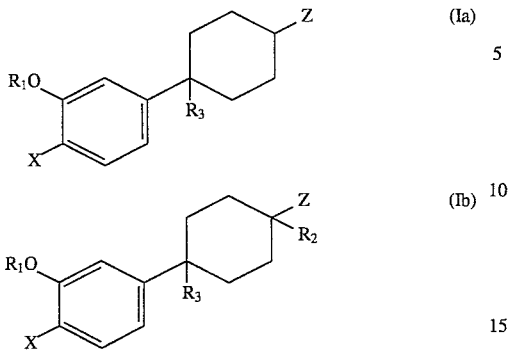

wherein:

$R_1$ is —$CH_2$-cyclopropyl, —$CH_2$-$C_{5-6}$ cycloalkyl, —$C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}$C(O)O$(CH_2)_{0-2}CH_3$, —$(CH_2)_{1-3}$O$(CH_2)_{0-2}CH_3$, and —$(CH_2)_{2-4}$OH;

m is 0 to 2;

n is 1 to 4;

r is 1 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, halogen, nitro, $NR_4R_5$, or formyl amine;

Y is O or $S(O)_{m'}$;

m' is 0, 1, or 2;

$R_2$ is —$CH_3$ or —$CH_2CH_3$ optionally substituted by 1 or more halogens;

$R_3$ is hydrogen, $C_{1-4}$ alkyl, $CH_2NHC(O)C(O)NH_2$, halo-substituted $C_{1-4}$ alkyl, CN, $CH_2OR_8$, C(Z')H, C(O)OR_8, C(O)NR_8R_{10}, or C≡$CR_8$;

Z' is O or $NOR_8$;

Z is $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(O)R_{14}$, $NR_{10}C(O)OR_7$, $NR_{10}C(O)NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), (1- or 2-imidazolyl), piperazinyl, morpholinyl, (2- or 3-thienyl), (4- or 5-thiazolyl), or phenyl;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

$R_{15}$ is $C(O)R_{14}$, $C(O)NR_4R_{14}$, $S(O)_2R_7$, or $S(O)_2NR_4R_{14}$;

provided that:
f) when Z is OH, X is $YR_2$, Y is oxygen, $X_2$ is oxygen, $X_3$ is hydrogen, s is 0, $R_2$ is $CH_3$ in $YR_2$, and $R_1$ is $CH_3$, then $R_3$ is other than CN or COOH;
g) when Z is OH, or $OCH_3$, $X_2$ is oxygen, $X_3$ is hydrogen, s is 0, and X is $YR_2$, then $R_3$ is other than H;
h) when Z is $S(O)_2C_{1-6}$ alkyl or $S(O)_2$ aryl, $X_2$ is oxygen, $X_3$ is hydrogen, s is 0, then $R_3$ is other than $OR_8$;
i) when $R_{12}$ is N-pyrazolyl, N-imidazolyl, N-triazolyl, N-pyrrolyl, N-piperazinyl, N-piperidinyl, or N-morpholinyl, then q is not 1;

or the pharmaceutically acceptable salts thereof.

Exemplified compounds of Formula (I) are:
cis-[4-cyano-4-(3-cyclopentyloxy-4-methoxyphenyl)cyclohexan-1-ol];
trans-[4-cyano-4-(3-cyclopentyloxy-4-methoxyphenyl)cyclohexan-1-ol];
cis-[4-cyano-4-(3-cyclopropylmethoxy-4-methoxyphenyl)cyclohexan-1-ol];
cis-[4-(3,4-bisdifluoromethoxyphenyl)-4-cyano-cyclohexan-1-ol];
trans-[4-cyano-4-(3-cyclopropylmethoxy-4-methoxyphenyl)cyclohexan-1-ol];
cis-[4-cyano-4-(3-cyclopropylmethoxy-4-difluoromethoxyphenyl)cyclohexan-1-ol];
trans-[4-cyano-4-(3-cyclopropylmethoxy-4-difluoromethoxyphenyl)cyclohexan-1-ol cis-[4-(3-cyclopentyloxy-4-methoxyphenyl)-4-ethynylcyclohexan-1-ol];

trans-[4-cyano-4-(3-cyclopentyloxy-4-methoxyphenyl)-1-formyloxycyclohexane];

trans-4-(3,4-bisdifluoromethoxyphenyl)-4-cyano-cyclohexan-1-ol;

trans-[4-(3,4-bisdifluoromethoxyphenyl)-4-cyano-1-formyloxycyclohexane];

cis-[4-(3,4-bisdifluoromethoxyphenyl)-4-cyano-1-methylcyclohexan-1-ol];

trans-[4-(3,4-bisdifluoromethoxyphenyl)-4-cyano-1-methylcyclohexan-1-ol];

cis-[4-cyano-4-(3-cyclopentyloxy-4-methoxyphenyl)cyclohexyl-1-amine];

trans-[4-cyano-4-(3-cyclopentyloxy-4-methoxyphenyl)cyclohexyl-1-amine];

cis-[4-(3,4-bisdifluoromethoxyphenyl)-4-cyanocyclohexyl-1-amine];

cis-[4-cyano-4-(3-cyclopropylmethoxy-4-methoxyphenyl)cyclohexyl-1-amine];

trans-[4-cyano-4-(3-cyclopropylmethoxy-4-methoxyphenyl)cyclohexyl-1-amine];

cis-[4-(3,4-bisdifluoromethoxyphenyl)-4-cyanocyclohexyl-1-(N,N-dimethyl)amine];

cis-[4-cyano-4-(3-cyclopropylmethoxy-4-methoxyphenyl)cyclohexyl-1-(N,N-dimethyl)amine];

cis-[4-(3,4-bisdifluoromethoxyphenyl)-4-cyanocyclohexyl-1-(N-methyl)amine];

trans-[4-(3,4-bisdifluoromethoxyphenyl)-4-cyanocyclohexyl-1-(N-methyl)amine];

trans-[4-cyano-4-(3-cyclopentyloxy-4-methoxyphenyl)-1-phthalimidocyclohexane];

trans-[4-(3,4-bisdifluoromethoxyphenyl)-4-cyano-1-phthalimidocyclohexane];

trans-[4-(3,4-bisdifluoromethoxyphenyl)-4-cyanocyclohexyl-1-amine];

trans-[1-N-(2-hydrazinocarbonylbenzamido)-4-(3,4-bisdifluommethoxyphenyl)-4-cyanocyclohexane];

cis-[4-cyano-4-(3-cyclopentyloxy-4-methoxyphenyl)-1-ureidocyclohexane];

cis-[4-(3,4-bisdifluoromethoxyphenyl)-4-cyano-1-ureidocyclohexane];

trans-[4-(3,4-bisdifluoromethoxyphenyl)-4-cyano-1-ureidocyclohexane];

cis-[4-cyano-4-(3-cyclopentyloxy-4-methoxyphenyl)-1-(N-hydroxyureido)cyclohexane];

trans-[4-cyano-4-(3-cyclopentyloxy-4-methoxyphenyl)-1-(N-hydroxyureido)cyclohexane];

cis-[4-cyano-4-(3-{4-fluorobenzyl}-4-methoxyphenyl)-1-(N-hydroxyureido)cyclohexane];

trans-[4-cyano-4-(3-{4-fluorobenzyl}-4-methoxyphenyl)-1-(N-hydroxyureido)cyclohexane];

cis-[4-cyano-4-(3-cyclopropylmethoxy-4-methoxyphenyl)-1-(N-hydroxyureido)cyclohexane];

trans-[4-cyano-4-(3-cyclopropylmethoxy-4-methoxyphenyl)-1-(N-hydroxyureido)cyclohexane];

cis-[1-acetamido-4-cyano-4-(3-cyclopentyloxy-4-methoxyphenyl)cyclohexane];

trans-[1-acetamido-4-(3,4-bisdifluoromethoxyphenyl)-4-cyanocyclohexane];

methyl N-{cis-[4-cyano-4-(3-cyclopentyloxy-4-methoxyphenyl)-cyclohexyl}-1-oxamate];

methyl N-{trans-[4-(3,4-bisdifluoromethoxyphenyl)-4-cyanocyclohexyl}-1-oxamate];

N-{cis-[4-cyano-4-(3-cyclopentyloxy-4-methoxyphenyl)cyclohexyl}-1-oxamide];

N-{trans-[4-(3,4-bisdifluoromethoxyphenyl)-4-cyanocyclohexyl}-1-oxamide];

N-{cis-[4-cyano-4-(3-cyclopentyloxy-4-methoxyphenyl)cyclohexyl}-1-oxamic acid];

cis-[4-cyano-4-(3-cyclopentyloxy-4-methoxyphenyl)-1-methoxycyclohexane];

trans-[4-cyano-4-(3-cyclopentyioxy-4-methoxyphenyl)-1-methoxycyclohexane]

cis-[4-cyano-4-(3-cyclopentyloxy-4-methoxyphenyl)-1-(N-hydroxyamino)cyclohexane];

trans-[4-cyano-4-(3-cyclopentyloxy-4-methoxyphenyl)-1-(N-hydroxyamino)cyclohexane];

cis-[4-cyano-4-(3-cyclopentyloxy-4-methoxyphenyl)-1-(N-hydroxyureido)cyclohexane]; and trans-[4-cyano-4-(3-cyclopentyloxy-4-methoxyphenyl)-1-(N-hydroxyureido)cyclohexane];

cis-[4-cyano-4-(3-{4-fluorobenzyl}-4-methoxyphenyl)-1-(N-hydroxyamino)cyclohexane];

trans-[4-cyano-4-(3-{4-fluorobenzyl}-4-methoxyphenyl)-1-(N-hydroxyamino)cyclohexane].

It will be recognized that some of the compounds of Formula (I) may exist in both racemic and optically active forms; some may also exist in distinct diastereomeric forms possessing distinct physical and biological properties. All of these compounds are considered to be within the scope of the present invention. Therefore another aspect of the present invention is the administration of either a racemate, a single enantiomeric form, a single diastereomeric form, or mixtures thereof.

The terms cis and trans denote stereochemistry at the C-1 position of the cyclohexane ring relative to the $R_3$ group at the C-4 position.

The term "$C_{1-3}$ alkyl", "$C_{1-4}$ alkyl", "$C_{1-6}$ alkyl" or "alkyl" ncludes both straight or branched chain radicals of 1 to 10, unless the chain length is limited thereto, including, but not limited to methyl, ethyl, n-propyl, isopropyl, n-butyl, sec-butyl, isobutyl, tert-butyl.

"Alkenyl" includes both straight or branched chain radicals of 1 to 6 carbon lengths, unless the chain length is limited thereto, including but not limited to vinyl, 1-propenyl, 2-propenyl, 2-propynyl, or 3-methyl-2-propenyl.

The term "cycloalkyl" or "cycloalkyl alkyl" includes 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain includes both straight or branched chain radicals of 1 to 4 carbon atoms.

"Heteroaryl" means an aromatic ring system containing one or more heteroatoms, such as imidazolyl, triazolyl, oxazolyl, pyridyl, pyrimidyl, pyrazolyl, pyrrolyl, furanyl, or thienyl.

"Halo" means chloro, fluoro, bromo, or iodo.

The term "inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses.

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferrably this cytokine is TNF-α.

All of the compounds of Formula (I) are useful in the method of inhibiting the production of TNF, preferably by macrophages, monocytes or macrophages and monocytes, in a mammal, including humans, in need thereof. All of the compounds of Formula (I) are useful in the method of inhibiting or mediating the enzymatic or catalytic activity of PDE IV and in treatment of disease states mediated thereby.

METHODS OF PREPARATION:

Preparing compounds of Formula (I) can be carried out by one of skill in the art according to the procedures outlined in the Examples, infra. The preparation of any remaining compounds of Formula (I) not described therein may be prepared by the analogous processes disclosed herein which comprise:

a) for compounds wherein $R_3$ is other than $C(=Z')H$ and wherein Z is OH, reacting a compound of Formula (2)

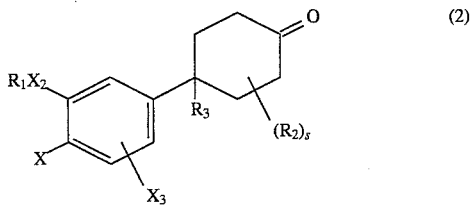

wherein $R_1$ represents $R_1$ as defined in relation to Formula (I) or a group convertable to $R_1$ and X and $X_3$ represent X and $X_3$ as defined in relation to Formula (I) or a group convertable to X or $X_3$ and $R_3$ represents $R_3$ as defined in relation to Formula (I) or a group convertable to $R_3$, with a suitable reducing agent, such as lithium borohydride, disiamylborane, lithium aluminum tris-(t-butoxide), or sodium borohydride, in a suitable non-reacting solvent, such as 1,2-dimethoxyethane, tetrahydrofuran or an alcohol, to provide compounds of Formula (I) wherein $R_3$ is other than $C(=Z')H$ and wherein Z is OH; preparation of such compounds of Formula (I) wherein $R_3$ is $C(=Z')H$ proceed in an analogous fashion from the compound of Formula (2) wherein $=Z'$ is an aldehyde protecting group, such as a dimethylacetal or a dioxolane, followed by deprotection to the aldehyde and subsequent elaboration by standard procedures known to those of skill in the art to the remaining compounds of Formula (I) wherein Z' is other than O.

For compounds wherein $R_3$ is other than $C(=Z')H$ and wherein Z is $NH_2$, $NHCH_3$, or $N(CH_3)_2$, reacting a compound of Formula (2) wherein $R_1$ represents $R_1$ as defined in relation to Formula (I) or a group convertable to $R_1$ and X and $X_3$ represent X and $X_3$ as defined in relation to Formula (I) or a group convertable to X or $X_3$ and $R_3$ represents $R_3$ as defined in relation to Formula (I) or a group convertable to $R_3$, with an ammonium salt, such as, for example, ammonium formate, methylamine hydrochloride, or dimethylamine hydrochloride, respectively, in the presence of a suitable reducing agent, such as sodium cyanoborohydride, in a suitable solvent, such as an alcohol, to provide compounds of Formula (I) wherein Z is $NH_2$, $NHCH_3$, or $N(CH_3)_2$, respectively; preparation of such compounds of Formula (I) wherein $R_3$ is $C(=Z')H$ proceed in an analogous fashion from the compound of Formula (2) wherein $=Z'$ is an aldehyde protecting group, such as a dimethylacetal or a dioxolane, followed by deprotection to the aldehyde and subsequent elaboration by standard procedures known to those of skill in the art to the remaining compounds of Formula (I) wherein Z' is other than O.

Alternatively, compounds of Formula (I) wherein Z is $NH_2$ may be prepared by reacting an appropriate alcohol of Formula (2) wherein Z is OH, $R_1$ represents $R_1$ as defined in relation to Formula (I) or a group convertable to $R_1$ and X and $X_3$ represent X and $X_3$ as defined in relation to Formula (I) or a group convertable to X or $X_3$ and $R_3$ represents $R_3$ as defined in relation to Formula (I) or a group convertable to $R_3$, with a complex of a phosphine, such as triphenyl phosphine, and an azodicarboxylate ester in the presence of an imide, such as phthalimide, followed by, e.g., hydrazinolysis in an alcoholic solvent.

Compounds of Formula (I) wherein Z is $SR_{14}$ may be prepared by reacting an appropriate compound of Formula (2) wherein Z is a leaving group, e.g., a mesylate, tosylate, chloride, or bromide, $R_1$ represents $R_1$ as defined in relation to Formula (I) or a group convertable to $R_1$ and X and $X_3$ represent X and $X_3$ as defined in relation to Formula (I) or a group convertable to X or $X_3$ and $R_3$ represents $R_3$ as defined in relation to Formula (I) or a group convertable to $R_3$, with a metal salt of a mercaptan, such as $NaSR_{14}$ in an appropriate aprotic solvent. Compounds of Formula (I) wherein Z is SH may be prepared by reacting an appropriate alcohol of Formula (2) wherein Z is OH with a complex of a phosphine, such as triphenyl phosphine, and an azodicarboxylate ester in the presence of thiolacetic acid, followed by hydrolysis of the resulting thioacetate.

Compounds of Formula (I) wherein Z is OH may be interconverted using the standard alcohol inversion procedures known in the art. It will be recognized that compounds of Formula (I) may exist in two distinct diastereomeric forms possessing distinct physical and biological properties; such isomers may be separated by standard chromatographic methods. Such isomers may be independently converted to the remaining compounds of Formula (I) wherein Z is other than OH, SH, and $NH_2$ by any of the wide variety of O, S, and N alkylation, sulfamidation, imidation, oxidation, or acylation procedures known to those of skill in the art.

For example, with proper manipulation of any chemically sensitive functional groups, compounds of Formula (1) wherein $NR_{13}R_{14}$ represent a ring, such as a 1- or 2-tetrazole, may be derived from reaction of an appropriate compound of Formula (I) wherein Z is a leaving group, e.g., a mesylate, tosylate, chloride or bromide, with the appropriate metal salt of $HNR_{13}R_{14}$, e.g., 5-($R_{14}$)-tetrazole; the appropriate compound of Formula (I) wherein Z is mesylate, tosylate, Br or Cl, derived in turn from the appropriate compound of Formula (1) wherein Z is OH.

Compounds of Formula (2) may be prepared in turn by the processes described in co-pending application P 50071.

The following sets of examples are provided to illustrate how to make and use this invention. They are not intended to limit the scope of the invention but are given for illustration purposes only.

SYNTHETIC EXAMPLES

Example 1

4-Cyano-4-(3-cyclopentyloxy-4-methoxyphenyl)cyclohexan-1-one (Intermediate of the Formula 2)

1a (3-Cyclopentyloxy-4-methoxyphenyl)acetonitrile

To a solution of 3-cyclopentyloxy-4-methoxybenzaldehyde (20 g, 90.8 mmol) in acetonitrile (100 mL) was added lithium bromide (15 g, 173 mmol) followed by the dropwise addition of trimethylsilylchloride (17.4 mL, 137 mmol). After 15 min, the reaction mixture was cooled to 0° C., 1,1,3,3-tetramethyldisiloxane (26.7 mL, 151 mmol) was added dropwise and the resulting mixture was allowed to warm to room temperature. After stirring for 3 h, the mixture was separated into two layers. The lower layer was removed, diluted with methylene chloride and filtered through Celite. The filtrate was concentrated under reduced pressure, dissolved in methylene chloride and refiltered. The solvent was removed in vacuo to provide a light tan oil. To a solution of this crude a-bromo-3-cyclopentyioxy-4-methoxytoluene in dimethylformamide (160 mL) under an argon atmosphere was added sodium cyanide (10.1 g, 206 mmol) and the resulting mixture was stirred at room temperature for 18 h, then poured into cold water (600 mL) and extracted three times with ether. The organic extract was washed three times with water, once with brine and was dried (potassium carbonate). The solvent was removed in vacuo and the residue was purified by flash chromatography, eluting with 10% ethyl acetate/hexanes, to provide an off-white solid (17.7 g, 84%): m.p. 32°–34° C.; an additional quantity (1.3 g) of slightly impure material also was isolated.

1b. Dimethyl 4-cyano-4-(3-cyclopentyloxy-4-methoxyphenyl)pimelate

To a solution of (3-cyclopentyloxy-4-methoxyphenyl)acetonitrile (7 g, 30.3 mmol) in acetonitrile (200 mL) under an argon atmosphere was added a 40% solution of Triton-B in methanol (1.4 mL, 3.03 mmol) and the mixture was heated to reflux. Methyl acrylate (27 mL, 303 mmol) was added carefully, the reaction mixture was maintained at reflux for 5 h and then cooled. The mixture was diluted with ether, was washed once with 1N hydrochloric acid and once with brine, was dried (magnesium sulfate) and the solvent was removed in vacuo. The solid residue was triturated with 5% ethanol/ hexane to provide a white solid (9 g, 74%): m.p. 81°–82° C.; and additional 1.1 g (9%) was also obtained from the filtrate.

Analysis Calc. for $C_{22}H_{29}NO_6$: C 65.49, H 7.25, N 3.47; found: C 65.47, H 7.11, N 3.49.

1c. 2-Carbomethoxy-4-cyano-4-(3-cyclopentyloxy-4-methoxyphenyl)cyclohexan-1-one

To a solution of dimethyl 4-cyano-4-(3-cyclopentyloxy-4-methoxyphenyl)pimelate (5.9 g, 14.6 mmol) in dry 1,2-dimethoxyethane (120 mL) under an argon atmosphere was added sodium hydride (80% suspension in mineral oil, 1.05 g, 43.8 mmol). The mixture was heated to reflux for 4.5 h, then was cooled to room temperature and was stirred for 16 h. Water was added and the reaction mixture was partitioned between ether and acidic water. The organic extract was dried (magnesium sulfate) and the solvent was removed in vacuo. The residue was purified by flash chromatography, eluting with 3:1 hexanes/ethyl acetate, to provide a white foam (4.9 g, 93%).

Analysis Calc. for $C_{19}H_{23}NO_3 \cdot \frac{1}{4}H_2O$: C 67.09, H 6.84, N 3.72; found: C 66.92, H 6.61, N 3.74.

1d. 4-Cyano-4-(3-cyclopentyloxy-4-methoxyphenyl)cyclohexan-1-one

A mixture of 2-carbomethoxy-4-cyano-4-(3-cyclopentyloxy-4-methoxyphenyl)cyclohexan-1-one (0.80 g, 2.15 mmol), dimethyl sulfoxide (16 mL), water (1 mL) and sodium chloride (0.8 g) under an argon atmosphere was heated at 140°–145° C. for 5 h. The reaction mixture was cooled and concentrated. The residue was purified by flash chromatography, eluting with 3:1 hexanes/ethyl acetate, to provide a yellow solid. Trituration with hexanes/ethyl acetate yielded a white solid (0.52 g, 77%): m.p. 111°–112° C.

Analysis Calc. for $C_{19}H_{23}NO_3$: C 72.82, H 7.40, N 4.47; found: C 72.72, H 7.39, N 4.48.

Example 2

4-(3,4-Bisdifluoromethoxyphenyl),4-cyanocyclohexan-1-one (Intermediate of the Formula 2)

2a. 3,4-Bisdifluoromethoxybenzaldehyde

A vigorously stirred mixture of 3,4-dihydroxybenzaldehyde (40 g, 290 mmol) and potassium carbonate (120 g, 870 mol) in dimethylformamide (500 mL) was heated under an atmosphere of chlorodifluoromethane at 80° C. for 7 h and then was stirred at room temperature overnight. The mixture was diluted with ether and was filtered. The filtrate was concentrated under reduced pressure, the residue was partitioned between ether and aqueous potassium carbonate and was extracted five times with ether. The organic extract was washed with aqueous potassium carbonate and dried (potassium carbonate). The solvent was removed in vacuo and the residue was purified by flash chromatography, eluting with 4:1 hexanes/ether to provide an oil (26.2 g, 38%).

2b. 3,4-Bisdifluoromethoxybenzyl alcohol 3,4-Bisdifluoromethoxybenzaldehyde (26.2 g, 110 mmol) in absolute ethanol (150 mL) was treated with sodium borohydride (8.32 g, 220 mmol) under an argon atmosphere at room temperature for 0.5 h. Ten percent aqueous sodium hydroxide (130 mL) was added, the ethanol was removed in vacuo, the mixture was partitioned between ether and water and was etracted twice with ether. The organic extract was dried (magnesium sulfate) and evaporated to a pale yellow oil (26.4 g, 100%).

2c. 2-(3,4-Bisdifluoromethoxyphenyl)acetonitrile

A solution of 3,4-bisdifluoromethoxybenzyl alcohol (26.4 g, 110 mmol) and pyridine (9.79 mL, 120 mmol) in chloroform (200 mL) under an argon atmosphere was treated with thionyl chloride (9.62 mL, 130 mmol) and the mixture was heated at reflux for 1 h. The solvent was removed, ether was added and the precipitate was removed by filtration. The filtrate was concentrated to a purple oil. To a solution of this 3,4-bisdifluoromethoxybenzyl chloride in dimethylformamide (200 mL) under an argon atmosphere was added sodium cyanide (11.86 g, 240 mmol). The resulting mixture was stirred and gently heated at 45° C. for 3 h, was cooled and was concentrated. The mixture was partitioned between ether and 5% aqueous sodium carbonate and was extracted five times with ether. The organic extract was washed once with brine, was dried (sodium carbonate) and the solvent was removed in vacuo to provide an oil (27 g).

2d. Dimethyl 4-cyano-4-(3,4-bisdifluoromethoxyphenyl)pimelate

To a solution of 2-(3,4-bisdifluoromethoxyphenyl)acetonitrile (27 g, 108 mmol) and a 40% solution of Triton-B in methanol (5 mL, 11 mmol) in acetonitrile (450 mL) under an argon atmosphere at room temperature was added methyl acrylate (48.6 mL, 540 mmol). After 20 min, aqueous hydrochloric acid (3N, 20 mL) was added and the mixture was concentrated. The residue was partitioned between water and ether, was extracted twice with ether, the ether layer was dried (magnesium sulfate) and evaporated in vacuo to provide a yellow oil (45.32 g, 99%).

2e. 2-Carbomethoxy-4-(3,4-bisdifluoromethoxyphenyl)-4-cyanocyclohexan-1-one

To a solution of dimethyl 4-(3,4-bisdifluoromethoxyphenyl)-4-cyanopimelate (45.32 g, 107 mmol) in dry 1,2-dimethoxyethane (450 mL) under an argon atmosphere was added sodium hydride (80% dispersion in mineral oil, 13 g, 432 mmol). The resulting mixture was refluxed for 1 h, was cooled to room temperature was quenched with water and was concentrated. The mixture was partitioned between ether and acidic brine, was extracted twice with ether, the organic layer was dried (magnesium sulfate) and the solvent was removed in vacuo. The residue was purified by flash chromatography, eluting with 3:1 hexanes/ethyl acetate, to provide a pale-orange oil (19.5 g, 46.6%).

Analysis Calc. for $C_{17}H_{15}F_4NO_5$: C 52.45, H 3.88, N 3.60; found: C 52.60, H 4.07, N 3.22.

2f. 4-(3,4-Bisdifluoromethoxyphenyl)-4-cyanocyclohexan-1-one

A mixture of 2-carbomethoxy-4-(3,4-bisdifluoromethoxyphenyl)-4-cyanocyclohexan-1-one (0.55 g, 1.4 mmole), dimethyl sulfoxide (8 mL), water (0.5 mL) and sodium chloride (0.5 g) under an argon atmosphere was heated at 140°–145° C. for 4 h. The reaction mixture was cooled to room temperature and concentrated. The residue was partitioned between ether and water, the organic layer was dried (magnesium sulfate) and the solvent was removed in vacuo. The product was purified by flash chromatography, eluting with 1:1 hexanes/ether. The residue was partitioned between water and ethyl acetate and the organic layer was evaporated to yield a yellow solid. Trituration from the minimal amount of ethyl acetate/hexanes provided a solid (0.3 g, 63.6%): m.p. 64°–66° C.

Analysis Calc. for $C_{15}H_{13}NO_3F_4$: C 54.39, H 3.96, N 4.23; found: C 54.25, H 3.96, N 4.20.

Examples 3 and 4 cis- and trans-[4-Cyano-4-(3-cyclopentyloxy-4-methoxyphenyl)cyclohexan-1-ol] cis-[4-Cyano-4-(3-cyclopentyloxy-4-methoxyphenyl)cyclohexan-1-ol]

To a solution of 4-cyano-4-(3-cyclopentyloxy-4-methoxyphenyl)cyclohexan-1-one (0.25 g, 0.8 mmol) in 1,2-dimethoxyethane (5 mL) under an argon atmosphere was added sodium borohydride (0.06 g, 1.6 mmol) and the mixture was stirred at room temperature for 0.25 h. Water was added, the mixture was partitioned between ethyl acetate and brine, the organic extract was dried (magnesium sulfate) and evaporated. Purification by flash chromatography, eluting with 1:1 hexanes/ethyl acetate, provided cis-[4-cyano-4-(3-cyclopentyloxy-4-methoxyphenyl)cyclohexan-1-ol] as a wax (0.2 g, 79%).

Analysis Calc. for $C_{19}H_{25}NO_3$: C 72.35, H 7.99, N 4.44; found: C 72.20, H 7.94, N 4.17.

trans-[-4-cyano-4-(3-cyclopentyloxy-4-methoxyphenyl)cyclohexan-1-ol] was also isolated from this procedure (0.05 g, 20% ).

Proceeding in the same manner, but substituting the appropriate intermediates for those described above the following compounds were made:

cis-[4-cyano-4-(3-cyclopropylmethoxy-4-methoxyphenyl) cyclohexan-1-ol]: m.p. 76° C.

Analysis Calc. for $C_{18}H_{23}NO_3$: C 71.73, H 7.69, N 4.65; found: C 71.41, H 7.55, N 4.56;

cis-[4-(3,4-bisdifluoromethoxyphenyl)-4-cyanocyclohexan-1-ol]: m.p. 48°–51° C.

Analysis Calc. for $C_{15}H_{15}F_4NO_3$: C 54.06, H 4.54, N 4.20; found: C 54.26, H 4.47, N 4.11;

trans-[4-Cyano-4-(3-cyclopropylmethoxy-4-methoxyphenyl)cyclohexan-1-ol]: oil.

Analysis Calc. for $C_{18}H_{23}NO_3 \cdot \frac{1}{4} H_2O$: C 70.68, H 7.74, N 4.58; found: C 70.97, H 7.56, N 4.59;

cis-[4-Cyano-4-(3-cyclopropylmethoxy-4-difluoromethoxyphenyl)cyclohexan-1-ol]: m.p. 58°–60° C.

Analysis Calc. for $C_{18}H_{21}F_2NO_3 \cdot \frac{1}{5} H_2O$: C 63.41, H 6.33, N 4.11; found: C 63.42, H 6.10, N 4.19;

trans-[4-Cyano-4-(3-cyclopropylmethoxy-4-difluoromethoxyphenyl)cyclohexan-1ol]: oil.

Analysis Calc. for $C_{18}H_{21}F_2NO_3 \cdot \frac{1}{5} H_2O$: C 63.41, H 6.33, N 4.11; found: C 63.43, H 6.12, N 3.89; and cis-[4-(3-Cyclopropylmethoxy-4-methoxyphenyl)-4-ethynylcyclohexan-1-ol]: m.p. 89°–90° C.

Analysis Calc. for $C_{20}H_{26}O_3 \cdot \frac{1}{8} H_2O$: C 75.86, H 8.35; found: C 75.94, H 8.35.

Example 5 trans-[4-Cyano-4-(3-cyclopentyloxy-4-methoxyphenyl)-1-formyloxycyclohexane].

cis-[4-Cyano-4-(3-cyclopentyloxy-4-methoxyphenyl)cyclohexan-1-ol] (0.2 g, 0.63 mmol), triphenylphosphine (0.17 g, 0.63 mmol) and formic acid (0.024 mL, 0.63 mmol) in freshly distilled tetrahydrofuran (10 mL) under an argon atmosphere at room temperature were stirred vigorously as diethylazodicarboxylate (0.1 mL, 0.63 mmol) was slowly added. After stirring in the dark for 18 h, an additional equivalent of each reagent was added and stirring was continued for 24 h. The liquids were removed under reduced pressure and the residue was purified by flash chromatography, eluting with 3:1 hexanes/ethyl acetate, to provide the trans-formate as an oil (0.15 g, 69%).

Example 6 trans-[4-Cyano-4-(3-cyclopentyloxy-4-methoxyphenyl)cyclohexan-1-ol]

trans-[4-Cyano-4-(3-cyclopentyloxy-4-methoxyphenyl)-1-formyloxycyclohexane] (0.12 g, 0.35 mmol) in ethyl acetate (2 mL) was treated with 10% aqueous sodium hydroxide (25 mL) at 60° C. for 5 h. The mixture was partitioned between ethyl acetate and water, the organic layer was dried (potassium carbonate) and the solvent was removed in vacuo. Purification by flash chromatography, eluting with 8% ethyl acetate/chloroform, provided the trans-alcohol as an oil (0.09 g, 82% ).

Analysis Calc. for $C_{19}H_{25}NO_3 \cdot \frac{1}{4} H_2O$: C 71.33, H 8.03, N 4.38; found: C 71.23, H 7.87, N 4.19.

Proceeding in the same manner, but substituting the approppriate intermediate, the following compound was made:

trans-4-(3,4-Bisdifluoromethoxyphenyl)-4-cyanocyclohexan-1-ol: oil.

Analysis Calc. for $C_{15}H_{15}F_4NO_3$: C 54.06, H 4.54, N 4.20; found: C 54.05, H 4.60, N 4.20.

Example 7 trans-[4-(3,4-Bisdifluoromethoxyphenyl)-4-cyano-1-formyloxycyclohexane]

cis-[4-(3,4-Bisdifluoromethoxyphenyl)-4-cyanocyclohexan-1-ol] (0.46 g, 1.38 mmol), triphenylphosphine (0.72 g, 2.76 mmol) and formic acid (0.104 mL, 2.76 mmol) in freshly distilled tetrahydrofuran (11 mL) under an argon atmosphere at room temperature were stirred vigorously as diethylazodicarboxylate (0.1 mL, 0.63 mmol) was slowly added. After stirring in the dark overnight, the liquids were removed under reduced pressure and the residue was purified by flash chromatography, eluting with 3:1 hexanes/ethyl acetate, to provide the trans-formate as an oil (0.41 g, 82%): m.p. 130°–131° C.

Analysis Calc. for $C_{16}H_{15}F_4NO_4$: C 53.19, H 4.18, N 3.88; found: C 53.03, H 3.99, N 4.12.

Examples 8 and 9 cis- and trans-[4-(3,4-Bisdifluoromethoxyphenyl)-4-cyano-1-methylcyclohexan-1-ol]

To a solution of trimethylaluminum (2M in toluene, 1.36 mL, 2.70 mmol) at room temperature under an argon atmosphere was added a solution of 4-(3,4-bisdifluoromethoxyphenyl)-4-cyanocyclohexan-1-one (0.3 g, 0.9 mmol). After 3.5 h, the mixture was cooled to 0° C. and saturated aqueous ammonium chloride solution was added. The mixture was extracted twice with methylene chloride, the organic extract was dried (magnesium sulfate) and evaporated. Purification by flash chromatography, eluting with 2:1 hexanes/ethyl acetate, provided trans-[4-(3,4-bisdifluoromethoxy-phenyl)-4-cyano-1-methylcyclohexan-1-ol] as a solid (0.12 g, 38%): m.p. 45°–47° C.

Analysis Calc. for $C_{16}H_{17}F_4NO_3$: C 55.33, H 4.93, N 4.03; found: C 55.27, H 4.96, N 3.93.

cis-[4-(3,4-Bisdifluoromethoxyphenyl)-4-cyano-1-methylcyclohexan-1-ol] was also isolated from this procedure as a solid (0.05 g, 16%): m.p. 46°–48° C.

Examples 10 and 11 cis- and trans-[4-Cyano-4-(3-cyclopentyloxy-4-methoxyphenyl)cyclohexyl-1-amine]

cis-[4-Cyano-4-(3-cyclopentyloxy-4-methoxyphenyl)cyclohexyl-1-amine]

To a solution of 4-cyano-4-(3-cyclopentyloxy-4-methoxyphenyl)cyclohexan-1-one (0.2 g, 0.64 mmol) and ammonium acetate (0.49 g, 6.4 mmol) in absolute ethanol (5 mL) under an argon atmosphere was added sodium cyanoborohydride (0.08 g, 1.28 mmol) and the mixture was stirred at room temperature for 4 h. Five percent aqueous sodium carbonate was added and the mixture was concentrated to near dryness. The residue was partitioned between ethyl acetate and basic brine, extracted twice more with ethyl acetate, the organic extract was dried (potassium carbonate) and evaporated. Purification by flash chromatography, eluting with 90:10:1 chloroform/methanol/water, provided cis-[4-cyano-4-(3-cyclopentyloxy-4-methoxyphenyl)cyclohexyl-1-amine] as a wax (0.1 g, 50%).

Analysis Calc. for $C_{19}H_{26}N_2O_2 \cdot \frac{1}{2}H_2O$: C 70.55, H 8.41, N 8.66; found: C 70.41, H 8.10, N 8.41.

trans-[4-Cyano-4-(3-cyclopentyloxy-4-methoxyphenyl)cyclohexyl-1-amine] was also isolated from this procedure as an oil (0.015 g, 7.5%). The trans-amine was also isolated as the minor product (5%) of a similar reaction conducted on a 2 g quantity of ketone.

Analysis Calc. for $C_{19}H_{26}N_2O_2 \cdot \frac{1}{2}H_2O$: C 70.55, H 8.41, N 8.66; found: C 70.71, H 8.28, N 8.45.

Proceeding in a similar manner, there were made:

cis-[4-(3,4-bisdifluoromethoxyphenyl)-4-cyanocyclohexyl-1-amine]: wax.

Analysis Calc. for $C_{15}H_{16}F_4N_2O_2$: C 54.22, H 4.85, N 8.43; found: C 53.98, H 4.79, N 8.30;

cis-[4-cyano-4-(3-cyclopropylmethoxy-4-methoxyphenyl)cyclohexyl-1-amine]: m.p. 84°–86° C.

Analysis Calc. for $C_{18}H_{24}N_2O_2$: C 71.97, H 8.05, N 9.33; found: C 71.67, H 7.79, N 9.10;

trans-[4-cyano-4-(3-cyclopropylmethoxy-4-methoxyphenyl)cyclohexyl-1-amine]: oil;

cis-[4-(3,4-bisdifluoromethoxyphenyl)-4-cyanocyclohexyl-1-(N,N-dimethyl)amine] (using dimethylamine hydrochloride in place of ammonium acetate) as an oil, which was converted to the hydrochloride salt: m.p. 228°–230° C.

Analysis Calc. for $C_{17}H_{20}F_4N_2O_2 \cdot HCl$: C 51.46, H 5.34, N 7.06; found: C 51.57, H 5.43, N 6.82;

cis-[4-cyano-4-(3-cyclopropylmethoxy-4-methoxyphenyl)cyclohexyl-1-(N,N-dimethyl)amine]: m.p. 85°–87° C.

Analysis Calc. for $C_{20}H_{24}N_2O_2 \cdot \frac{1}{2}H_2O$: C 71.18, H 8.66, N 8.30; found: C 71.09, H 8.54, N 8.53;

cis-[4-(3,4-bisdifluoromethoxyphenyl)-4-cyanocyclohexyl-1-(N-methyl)amine]: oil.

Analysis Calc. for $C_{16}H_{18}F_4N_2O_2 \cdot \frac{1}{10}H_2O$: C 55.20, H 5.27, N 8.05; found: C 55.08, H 5.14, N 7.90; and trans-[4-(3,4-bisdifluoromethoxyphenyl)-4-cyanocyclohexyl-1-(N-methyl)amine]: oil.

Analysis Calc. for $C_{16}H_{18}F_4N_2O_2$: C 55.49, H 5.24, N 8.09; found: C 55.20, H 5.30, N 7.91.

Example 12 trans-[4-Cyano-4-(3-cyclopentyloxy-4-methoxyphenyl)-1-phthalimidocyclohexane]

cis-[4-Cyano-4-(3-cyclopentyloxy-4-methoxyphenyl)cyclohexan-1-ol] (0.2 g, 0.63 mmol), triphenylphosphine (0.166 g, 0.63 mmol) and phthalimide (0.093 g, 0.63 mmol) in freshly distilled tetrahydrofuran (10 mL) under an argon atmosphere at room temperature were stirred vigorously with diethylazodicarboxylate (0.1 mL, 0.63 mmol) in the dark overnight. The liquids were removed under reduced pressure, with purification by flash chromatography, eluting with 3:1 hexanes/ethyl acetate, providing the trans-phthalimide as a solid (0.12 g, 42%): m.p. 130°–131° C.

Analysis Calc. for $C_{27}H_{28}N_2O_4 \cdot \frac{1}{4}H_2O$: C 72.22, H 6.40, N 6.24; found: C 72.18, H 6.35, N 6.27.

Proceeding in a similar manner, the following compound was made:

trans-[4-3,4-Bisdifluoromethoxyphenyl)-4-cyano-1-phthalimidocyclohexane]: m.p. 38°–42° C.

Analysis Calc. for $C_{23}H_{18}F_4N_2O_4$: C 59.74, H 3.92, N 6.06; found: C 59.62, H 4.15, N 5.96.

Example 13 trans-[4-(3,4-Bisdifluoromethoxyphenyl)-4-cyanocyclohexyl-1-amine]

A solution of trans-[4-(3,4-bisdifluoromethoxyphenyl)-4-cyano-1-phthalimidocyclohexane] (0.55 g, 1.19 mmol) in ethanol (30 mL) was treated with hydrazine monohydrate (0.06 mL, 1.19 mmol) at room temperature under an argon atmosphere for 1.5 h and then heated at reflux for 2.5 h. The mixture was allowed to cool, the solid was removed by filtration and the filtrate was concentrated. Purification by flash chromatography, eluting with 90:10:1 chloroform/ methanol water, provided the trans-amine as an oil (0.21g, 53%).

Analysis Calc. for $C_{15}H_{16}F_4N_2O_2 \cdot \frac{1}{8}H_2O$: C 53.85, H 4.90, N 8.37; found: C 53.69, H 4.82, N 8.11.

Proceeding in a similar manner but maintaining room temperature rather than reflux, the following compound was made:

trans-[1-N-(2-Hydrazinocarbonylbenzamido)-4-(3,4-bisdifluoromethoxyphenyl)-4-cyanocyclohexane]: m.p: 153°–155° C.

Analysis Calc. for $C_{23}H_{22}F_4N_4O_4$: C 55.87, H 4.49, N 11.33; found: C 55.99, H 4.38, N 11.04.

Example 14 cis-[4-Cyano-4-(3-cyclopentyloxy-4-methoxyphenyl)-1-ureidocyclohexane]

A solution of cis-[4-cyano-4.(3-cyclopentyloxy-4-methoxyphenyl)cyclohexyl-1amine] (0.1 g, 0.32 mmol) and trimethylsilyl isocyanate (0.08 mL, 0.48 mmol) in tetrahydrofuran (1.6 mL) was heated at reflux under an argon atmosphere for 5 h. The mixture was allowed to cool, was partitioned between methylene chloride and acidic water, the organic extract was dried (potassium carbonate) and evaporated. The product was triturated with methylene chloride to provided a yellow solid (0.08 g, 72%): m.p. 273° C.

Analysis Calc. for $C_{20}H_{27}N_3O_3$: C 67.20, H 7.61, N 11.75; found: C 67.08, H 7.23, N 11.52.

Proceeding in a similar manner, the following compounds were made:

cis-[4-(3,4-bisdifluoromethoxyphenyl)-4-cyano-1-ureidocyclohexane]: m.p. 124°–125° C.

Analysis Calc. for $C_{16}H_{17}F_4N_3O_3 \cdot \frac{1}{4} H_2O$: C 50.59, H 4.64, N 11.06; found: C 50.59, H 4.42, N 10.83;

trans-[4-(3,4-bisdifluoromethoxyphenyl)-4-cyano-1-ureidocyclohexane]: m.p. 161°–162° C.;

cis-[4-cyano-4-(3-cyclopentyloxy-4-methoxyphenyl)-1-(N-hydroxyureido)cyclohexane]: m.p. 108°–109° C.

Analysis Calc. for $C_{20}H_{27}N_3O_4 \cdot 0.4 H_2O$: C 63.11, H 7.36, N 11.04; found: C 63.15, H 7.36, N 10.81;

trans-[4-cyano-4-(3-cyclopentyloxy-4-methoxyphenyl)-1-(N-hydroxyureido)cyclohexane]: m.p. 102°–103° C.

Analysis Calc. for $C_{20}H_{27}N_3O_4 \cdot \frac{1}{4} H_2O$: C 60.25, H 7.18, N 10.51; found: C 60.33, H 7.07, N 10.41;

cis-[4-cyano-4-(3-{4-fluorobenzyl}-4-methoxyphenyl)-1-(N-hydroxyureido)cyclohexane]: m.p. 83°–85° C.

Analysis Calc. for $C_{22}H_{24}FN_3O_4 \cdot 0.85 H_2O$: C 61.63, H 6.04, N 9.80; found: C 61.81, H 5.82, N 9.75;

trans-[4-cyano-4-(3-{4-fluorobenzyl}-4-methoxyphenyl)-1-(N-hydroxyureido)cyclohexane]: m.p. 87°–89° C.

Analysis Calc. for $C_{22}H_{24}FN_3O_4 \cdot 0.85 H_2O$: C 61.63, H 6.04, N 9.80; found: C 61.64, H 5.76, N 9.69;

cis-[4-cyano-4-(3-cyclopropylmethoxy-4-methoxyphenyl)-1-(N-hydroxyureido)cyclohexane]: m.p. 181°–182° C.

Analysis Calc. for $C_{19}H_{25}N_3O_4 \cdot \frac{2}{3} H_2O$: C 61.44, H 7.15, N 11.31; found: C 61.57, H 6.81, N 11.14; and trans-[4-cyano-4-(3-cyclopropylmethoxy-4-methoxyphenyl)-1-(N-hydroxyureido)cyclohexane]: m.p. 137°–138° C.

Analysis Calc. for $C_{19}H_{25}N_3O_4 \cdot \frac{1}{4} H_2O$: C 62.71, H 7.06, N 11.55; found: C 62.80, H 6.82, N 11.31.

Example 15 cis-[1-Acetamido-4-cyano-4-(3-cyclopentyloxy-4-methoxyphenyl)cyclohexane]

To a solution of cis-[4-cyano-4-(3-cyclopentyloxy-4-methoxyphenyl)cyclohexyl-1-amine] (0.1 g, 0.32 mmol) in methylene chloride (2 mL) at 0° C. under an argon atmosphere was added methyl amine (0.044 mL, 0.32 mmol), 4-N,N-dimethylaminopyridine (0.04 g, 0.32 mmol) and acetic anhydride (0.06 mL, 0.64 mmol) and the mixture was allowed to warm slowly to room temperature. After 4.5 h, the mixture was partitioned between methylene chloride and acidic water extracted twice with methylene chloride, the organic extract was dried (potassium carbonate) and evaporated. Purification by flash chromatography, eluting with 5% methanol/chloroform, provided a white solid (0.11 g, 96%): m.p. 277°–278° C.

Analysis Calc. for $C_{21}H_{28}N_2O_3$: C 70.75, H 7.91, N 7.85; found: C 70.61, H 7.82, N 7.51.

Proceeding in a similar manner, the following compound was made:

trans-[1-acetamido-4-(3,4-bisdifluoromethoxyphenyl)-4-cyanocyclohexane] (conducted in the absence of methylamine and 4-N,N-dimethylaminopyridine): wax.

Analysis Calc. for $C_{17}H_{18}F_4N_2O_3$: C 54.55, H 4.85, N 7.48; found: C 54.35, H 4.81, N 7.27.

Example 16

Methyl N-{cis-[4-cyano-4-(3-cyclopentyloxy-4-methoxyphenyl)cyclohexyl]-1-oxamate}

To a solution of cis-[4-cyano-4-(3-cyclopentyloxy-4-methoxyphenyl)cyclohexyl-1-amine] (0.08 g, 0.25 mmol) and methylamine (0.039 mL, 0.27 mmol) in methylene chloride (1.6 mL) at 0° C. under an argon atmosphere was added methyl oxalyl chloride (0.29 mL, 0.25 mmol). After 0.25 h, the mixture was partitioned between methylene chloride and acidic water, extracted twice with methylene chloride, the organic extract was dried (potassium carbonate) and evaporated. Purification by flash chromatography, eluting with 5% ethyl acetate/methylene chloride, provided a white solid (0.09 g, 90%).

In a similar manner there was prepared:

Methyl N-{trans-[4-(3,4-bisdifluoromethoxyphenyl)-4-cyanocyclohexyl]-1oxamate]: oil.

Example 17

N-{cis-[4-Cyano-4-(3-cyclopentyloxy-4-methoxyphenyl)cyclohexyl]-1-oxamide}

Into a solution of methyl N-{cis-[4-cyano-4-(3-cyclopentyloxy-4-methoxyphenyl)cyclohexyl}oxamate] (0.06 g, 0.15 mmol) in methanol (3 mL) contained in a pressure vessel at −78° C. was condensed anhydrous ammonia (3 mL). The vessel was sealed, was allowed to come to room temperature and was stirred overnight. The vessel was cooled to −78° C., was opened and the ammonia was allowed to evaporate at room temperature. The mixture was partitioned between chloroform and water, extracted twice with chloroform, the organic extract was dried (potassium carbonate) and evaporated. Trituration of the product with methylene chloride/ether provided a white solid (0.05 g, 88%): m.p. >215° C.

Analysis Calc. for $C_{21}H_{27}N_3O_4$: C 65.44, H 7.06, N 10.90; found: C 65.24, H 6.77, N 10.72.

In a similar manner there was prepared:

N-{trans-[4-(3,4-Bisdifluoromethoxyphenyl)-4-cyanocyclohexyl}oxamide]: m.p. 130°–131° C.

Analysis Calc. for $C_{17}H_{17}F_4N_3O_4$: C 50.63, H 4.25, N 10.42; found: C 50.77, H 4.32, N 10.33.

Example 18

N-{cis-[4-Cyano-4-(3-cyclopentyloxy-4-methoxyphenyl)cyclohexyl]-1-oxamic acid}

A solution of methyl N-{cis-[4-cyano-4-(3-cyclopentyloxy-4-methoxyphenyl)cyclohexyl]-1-oxamate] (0.05 g, 0.12 mmol) in methanol (1 mL), tetrahydrofuran (1 mL) and water at room temperature was stirred with a pellet of sodium hydroxide for 3 h. The solvents were removed, the residue was dissolved in methanol and was acidified with 3N hydrochloric acid. The solid was collected and washed with ether to provide a white solid (0.03 g, 62%): m.p. 78°–83° C.

Analysis Calc. for $C_{17}H_{16}F_4N_2O_5 \cdot H_2O$: C 48.34, H 4.30, N 6.63; found: C 48.34, H 4.30, N 6.46.

Example 19 cis-[4-Cyano-4-(3-cyclopentyloxy-4-methoxyphenyl)-1-methoxycyclohexane]

cis-[4-Cyano-4-(3-cyclopentyloxy-4-methoxyphenyl)cyclohexan-1-ol] (0.17 g, 0.5 mmol), methyl iodide (1 mL) and silver oxide (0.19 g, 0.8 mmol) in acetonitrile (1 mL) under an argon atmosphere were refluxed in the dark overnight. The mixture was cooled, the solid was removed by filtration and the filtrate was evaporated The residue was purified by flash chromatography, eluting with 2:1 hexanes/ethyl acetate, to provide an oil (0.12 g, 66%).

Analysis Calc. for $C_{16}H_{17}F_4NO_3$: C 55.33, H 4.93, N 4.03; found: C 55.33, H 4.91, N 3.77.

In a similar manner there was prepared:
trans-[4-Cyano-4-(3-cyclopentyloxy-4-methoxyphenyl)-1-methoxycyclohexane]: oil.

Analysis Calc. for $C_{16}H_{17}F_4NO_3$: C 55.33, H 4.93, N 4.03; found: C 55.44, H 4.86, N 3.97.

Examples 20 and 21 cis- and trans-[4-Cyano-4-(3-cyclopentyloxy-4-methoxyphenyl)-1-(N-hydroxyamino)cyclohexane]

To a solution of 4-cyano-4-(3-cyclopentyloxy-4-methoxyphenyl)cyclohexan-1-one-oxime (0.42 g, 1.27 mmol) and a trace of methyl orange in methanol (5 mL) at room temperature under an argon atmosphere was added in one portion sodium cyanoborohydride (0.054 g, 0.85 mmol) followed immediately by the dropwise addition of hydrogen chloride-saturated methanol to attain and maintain a deep red color. After 1.5 h, water and 15% aqueous sodium hydroxide (to pH>9) were added, the mixture was extracted three times with methylene chloride, the organic extract was dried (potassium carbonate) and evaporated. Purification by flash chromatography, eluting with 50% ethyl acetate/hexanes, provided the cis isomer as a white solid (0.11 g, 27%): m.p. 103°–104° C.

Analysis Calc. for $C_{19}H_{26}N_2O_3 \cdot \frac{1}{4}H_2O$: C 68.14, H 7.98, N 8.36; found: C 67.95, H 7.81, N 8.23. Also isolated was the trans isomer as a white solid (0.08 g, 20%): m.p. 150°–151° C.

Analysis Calc. for $C_{19}H_{26}N_2O_3 \cdot \frac{1}{4} H_2O$: C 68.14, H 7.98, N 8.36; found: C 68.22, H 7.81, N 8.20.

In a similar manner there were prepared:
cis-[4-cyano-4-(3-cyclopropylmethoxy-4-methoxyphenyl)-1-(N-hydroxyamino)cyclohexane]: foam.

Analysis Calc. for $C_{18}H_{24}N_2O_3 \cdot \frac{1}{4} H_2O$: C 67.37, H 7.69, N 8.73: found: C 67.09, H 7.45, N 8.45;
trans-[4-cyano-4-(3-cyclopropylmethoxy-4-methoxyphenyl)-1-(N-hydroxyamino)cyclohexane]: m.p. 142.5°–144.5° C.

Analysis Calc. for $C_{18}H_{24}N_2O_3 \cdot \frac{1}{4} H_2O$: C 67.37, H 7.69, N 8.73; found: C 67.26, H 7.47, N 8.33;
cis-[4-cyano-4-(3-{4-fluorobenzyl}-4-methoxyphenyl)-1-(N-hydroxyamino)cyclohexane]: m.p. 118°–120° C.

Analysis Calc. for $C_{21}H_{23}FN_2O_3 \cdot 0.45 H_2O$: C 66.63, H 6.36, N 7.40; found: C 66.63, H 6.26, N 7.22; and
trans-[4-cyano-4-(3-{4-fluorobenzyl}-4-methoxyphenyl)-1-(N-hydroxyamino)cyclohexane]: m.p. 135°–136° C.

METHODS OF TREATMENT

In order to use a compound of Formula (I) or a pharmaceutically acceptable salt thereof for the treatment of humans and other mammals, it is normally formulated in accordance with standard pharmaceutical practice as a pharmaceutical composition. The compounds of Formula (I) or a pharmaceutically acceptable salt thereof can be used in the manufacture of a medicament for the prophylatic or therapeutic treatment of any disease state in a human or other mammal which is mediated by inhibition of PDE IV, such as but not limited to asthma, allergic, or inflammatory diseases. The compounds of Formula (I) are administered in an amount sufficient to treat such a disease in a human or other mammal.

The method of treatment and monitoring for an HIV-infected human manifesting immune dysfunction or cytokine-mediated disease associated problems is taught in Hanna, WO 90/15534, Dec. 27, 1990. In general, an initial treatment regimen can be copied from that known to be effective in interfering with TNF activity for other TNF mediated disease states by the compounds of Formula (I). Treated individuals will be regularly checked for T cell numbers and T4/T8 ratios and/or measures of viremia such as levels of reverse transcriptase or viral proteins, and/or for progression of monokine-mediated disease associated problems such as cachexia or muscle degeneration. If no effect is seen following the normal treatment regimen, then the amount of the monokine activity interfering agent administered is increased, e.g., by fifty percent per week.

The pharmaceutical composition of the present invention will comprise an effective, non-toxic amount of a compound of Formula (I) and a pharmaceutically acceptable carrier or diluent. The compounds of Formula (I) are administered in conventional dosage forms prepared by combining a compound of Formula (I) in an amount sufficient to produce TNF production inhibiting activity, respectively, with standard pharmaceutical carriers according to conventional procedures. These procedures may involve mixing, granulating, and compressing or dissolving the ingredients as appropriate to the desired preparation.

Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates, or oils and are incorporated in a soft gelatin capsule shell. A syrup formulation will generally consist of a suspension or solution of the compound or salt in a liquid carrier for example, ethanol, glycerine, or water with a flavoring or coloring agent.

The daily dosage regimen for oral administration is suitably about 0.001 mg/kg to 100mg/kg, preferably 0.01 mg/Kg to 40 mg/Kg, of a compound of Formula (I) or a pharmaceutically acceptable salt thereof calculated as the free base. The active ingredient may be administered from 1 to 6 times a day, sufficient to exhibit activity.

While it is possible for an active ingredient to be administered neat, it is preferable to present it as a pharmaceutical formulation. The active ingredient may comprise, for topical administration, from 0.001% to 10% w/w, e.g., from 1% to 2% by weight of formulation, although it may comprise as much as 10% w/w but preferably not in excess of 5% w/w and more preferably from 0.1% to 1% w/w of Formulation.

Formulations of the present invention comprise an active ingredient together with one or more acceptable carrier(s) thereof and optionally any other therapeutic ingredient(s). The carrier(s) must be 'acceptable' in the sense of being compatible with the other ingredients of Formulation and not deleterious to the recipient thereof.

It will be recognized by one of skill in the an that the form and character of the pharmaceutically acceptable carrier or diluent is dictated by the amount of active ingredient with which it is to be combined, the mute of administration, and other well-known variables.

UTILITY EXAMPLES

Example A

Inhibitory effect of compounds of Formula (I) on in vitro TNF production by human monocytes The inhibitory effect of compounds of Formula (I) on in vitro TNF production by human monocytes may be determined by the protocol as described in Badger et at., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I). The protocol used in these models is described in Badger et al., EPO published Application 0 411 754 A2, Feb. 6, 1991, and in Hanna, WO 90/15534, Dec. 27, 1990.

The exemplified compounds herein demonstrated a positive in vivo response in reducing serum levels of TNF induced by the injection of endotoxin.

No toxic effects are expected when these compounds are administered in accordance with the present invention.

Example C

Isolation of PDE Isozymes

The phosphodiesterase inhibitory activity and selectivity of the compounds of Formula (I) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798-1804, 1992].

Phosphodiesterase activity is assayed as described in the protocol of Torphy and Cieslinski, Mol. Pharmacol., 37:206–214, 1990. Positive $IC_{50}$'s in the nanomolar to µM range for compounds of the workings examples described herein for Formula (I) have been demonstrated.

Example D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 µM) of PDE inhibitors for one minute and 1 µM prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general protocol for this assay is described in Brooker et al., Radioimmunassay of cyclic AMP and cyclic GMP., Adv. Cyclic Nucleotide Res., 10:1–33, 1979. The compounds of the working examples as described herein for Formula (I) have demonstrated a positive $EC_{50}$s in the µM range in the above assay.

What is claimed is:

1. A compound of Formula (I):

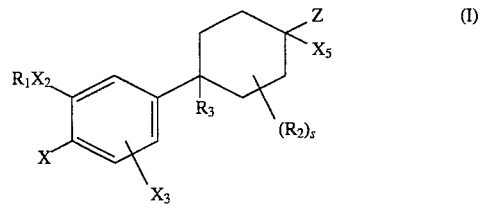

wherein:

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, $C_{3-6}$ cycloalkyl, or a $C_{4-6}$ cycloalkyl containing one or two unsaturated bonds, wherein the cycloalkyl moiety may be optionally substituted by 1 to 3 methyl groups or one ethyl group;

provided that:

a) when $R_6$ is hydroxyl, then m is 2; or b) when $R_6$ is hydroxyl, then r is 2 to 6; or c) when n is 1 and m is 0, then $R_6$ is other than H in $-(CR_4R_5)_nO(CR_4R_5)_mR_6$;

X is $YR_2$, halogen, nitro, $NR_4R_5$, or formyl amine;

Y is O;

m' is a number having a value of 0, 1, or 2;

$X_2$ is O or $NR_8$;

$X_3$ is hydrogen or X;

$R_2$ is independently selected from $-CH_3$ or $-CH_2CH_3$ optionally substituted by 1 or more halogens;

s is 0 to 4;

$R_3$ is CN or C≡$R_8$;

Z is $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

Y' is O;

$R_7$ is $—(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$;

q is 0, 1, or 2;

$R_{12}$ is $C_{3-7}$ cycloalkyl, naphthyl, or phenyl;

$R_8$ is independently selected from hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{14}$ is hydrogen or $R_7$;

$R_{15}$ is $C(O)R_{14}$, $C(O)NR_4R_{14}$, $S(O)_2R_7$, or $S(O)_2NR_4R_{14}$;

or the pharmaceutically acceptable salts thereof.

2. A compound of claim 1 wherein
$R_1$ is —$CH_2$-cyclopropyl, cyclopentyl, methyl or $CF_2H$;
$R_3$ is CN;
X is $YR_2$;
Y is O;
$X_2$ is oxygen; and
$X_3$ is hydrogen.

3. A compound of claim 1 which is:
cis-[4-cyano-4-(3-cyclopentyloxy-4-methoxyphenyl)cyclohexan-1-ol];
trans-[4-cyano-4-(3-cyclopentyloxy-4-methoxyphenyl)cyclohexan-1-ol];
cis-[4-cyano-4-(3-cyclopropylmethoxy-4-methoxyphenyl)cyclohexan-1-ol];
cis-[4-(3,4-bisdifluoromethoxyphenyl)-4-cyano-cyclohexan-1-ol];
trans-[4-cyano-4-(3-cyclopropylmethoxy-4-methoxyphenyl)cyclohexan-1-ol];
cis-[4-cyano-4-(3-cyclopropylmethoxy-4-difluoromethoxyphenyl)cyclohexan-1-ol];
trans-[4-cyano-4-(3-cyclopropylmethoxy-4-difluoromethoxyphenyl)cyclohexan-1-ol];
cis-[4-(3-cyclopentyloxy-4-methoxyphenyl)-4-ethynylcyclohexan-1-ol];
trans-[4-cyano-4-(3-cyclopentyloxy-4-methoxyphenyl)-1-formyloxycyclohexane];
trans-4-(3,4-bisdifluoromethoxyphenyl)-4-cyano-cyclohexan-1-ol;
trans-[4-(3,4-bisdifluoromethoxyphenyl)-4-cyano-1-formyloxycyclohexane];
cis-[4-(3,4-bisdifluoromethoxyphenyl)-4-cyano-1-methylcyclohexan-1-ol];
trans-[4-(3,4-bisdifluoromethoxyphenyl)-4-cyano-1-methylcyclohexan-1-ol];
cis-[4-cyano-4-(3-cyclopentyloxy-4-methoxyphenyl)cyclohexyl-1-amine];
trans-[4-cyano-4-(3-cyclopentyloxy-4-methoxyphenyl)cyclohexyl-1-amine];
cis-[4-(3,4-bisdifluoromethoxyphenyl)-4-cyanocyclohexyl-1-amine];
cis-[4-cyano-4-(3-cyclopropylmethoxy-4-methoxyphenyl)cyclohexyl-1-amine];
trans-[4-cyano-4-(3-cyclopropylmethoxy-4-methoxyphenyl)cyclohexyl-1-amine];
cis-[4-(3,4-bisdifluoromethoxyphenyl)-4-cyanocyclohexyl-1-(N,N-dimethyl)amine];
cis-[4-cyano-4-(3-cyclopropylmethoxy-4- methoxyphenyl)cyclohexyl-1-(N-N-dimethyl)amine];
cis-[4-(3,4-bisdifluoromethoxyphenyl)-4-cyanocyclohexyl-1-(N-methyl)amine];
trans-[4-(3,4-bisdifluoromethoxyphenyl)-4-cyanocyclohexyl-1-(N-methyl)amine];
trans-[4-cyano-4-(3-cyclopentyloxy-4-methoxyphenyl)-1-phthalimidocyclohexane];
trans-[4-(3,4-bisdifluoromethoxyphenyl)-4-cyano-1-phthalimidocyclohexane];
trans-[4-(3,4-bisdifluoromethoxyphenyl)-4-cyanocyclohexyl-1-amine];
trans-[1-N-(2-hydrazinocarbonylbenzamido)-4-(3,4-bisdifluoromethoxyphenyl)-4-cyanocyclohexane];
cis-[4-cyano-4-(3-cyclopentyloxy-4-methoxyphenyl)-1-ureidocyclohexane];
cis-[4-(3,4-bisdifluoromethoxyphenyl)-4-cyano-1-ureidocyclohexane];
trans-[4-(3,4-bisdifluoromethoxyphenyl)-4-cyano-1-ureidocyclohexane];
cis-[4-cyano-4-(3-cyclopentyloxy-4-methoxyphenyl)-1-(N-hydroxyureido)-cyclohexane];
trans-[4-cyano-4-(3-cyclopentyloxy-4-methoxyphenyl)-1-(N-hydroxyureido)cyclohexane];
cis-[4-cyano-4-(3-{4-fluorobenzyl}-4-methoxyphenyl)-1-(N-hydroxyureido)-cyclohexane];
trans-[4-cyano-4-(3-{4-fluorobenzyl}-4-methoxyphenyl)-1-(N-hydroxyureido)cyclohexane];
cis-[4-cyano-4-(3-cyclopropylmethoxy-4-methoxyphenyl)-1-(N-hydroxyureido)cyclohexane];
trans-[4-cyano-4-(3-cyclopropylmethoxy-4-methoxyphenyl)-1-(N-hydroxyureido)cyclohexane];
cis-[1-acetamido-4-cyano-4-(3-cyclopentyloxy-4-methoxyphenyl)cyclohexane];
trans-[1-acetamido-4-(3,4-bisdifluoromethoxyphenyl)-4-cyanocyclohexane];
methyl N-{cis-[4-cyano-4-(3-cyclopentyloxy-4-methoxyphenyl)-cyclohexyl]-1-oxamate};
methyl N-{trans-[4-(3,4-bisdifluoromethoxyphenyl)-4-cyanocyclohexyl]-1-oxamate};
N-{cis-[4-cyano-4-(3-cyclopentyloxy-4-methoxyphenyl)cyclohexyl]-1-oxamide};
N-{trans-[4-(3,4-bisdifluoromethoxyphenyl)-4-cyanocyclohexyl]-1-oxamide};
N-{cis-[4-cyano-4-(3-cyclopentyloxy-4-methoxyphenyl)cyclohexyl]-1-oxamic acid};
cis-[4-cyano-4-(3-cyclopentyloxy-4-methoxyphenyl)-1-methoxycyclohexane];
trans-[4-cyano-4-(3-cyclopentyloxy-4-methoxyphenyl)-1-methoxycyclohexane]
cis-[4-cyano-4-(3-cyclopentyloxy-4-methoxyphenyl)-1-(N-hydroxyamino)-cyclohexane];
trans-[4-cyano-4-(3-cyclopentyloxy-4-methoxyphenyl)-1-(N-hydroxyamino)-cyclohexane];
cis-[4-cyano-4-(3-cyclopentyloxy-4-methoxyphenyl)-1-(N-hydroxyureido)-cyclohexane];

trans-[4-cyano-4-(3-cyclopentyloxy-4-methoxyphenyl)-1-(N-hydroxyureido)cyclohexane];
cis-[4-cyano-4-(3-{4-fluorobenzyl}-4-methoxyphenyl)-1-(N-hydroxyamino)-cyclohexane];
or
trans-[4-cyano-4-(3-{4-fluorobenzyl}-4-methoxyphenyl)-1-(N-hydroxyamino)cyclohexane].

4. A pharmaceutical composition comprising a compound of Formula (I) according to claim 1 and a pharmaceutically acceptable excipient.

5. A method for treating an allergic or inflammatory disease which method comprises administering to a subject in need thererof an effective maount of a compound of Formula (I) according to claim 1 alone or in combination with a pharmaceutically acceptable excipient.

6. A method for inhibiting the production of tumor necrosis factor which comprises administering to a subject in need thereof an effective amount of a compound of Formula (I) according to claim 1 alone or in combination with a pharmaceutically acceptable excipient.

* * * * *